United States Patent
Breton et al.

(10) Patent No.: US 9,125,934 B2
(45) Date of Patent: *Sep. 8, 2015

(54) BACTERIAL EXTRACTS CULTURED IN THERMAL WATERS FOR TREATING SENSITIVE SKIN, MUCOUS MEMBRANES AND SCALPS

(75) Inventors: Lionel Breton, Versailles (FR); Yann Mahe, Sainte Genevieve des Bois (FR); Richard Martin, Rochecorbon (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/175,129

(22) Filed: Jul. 17, 2008

(65) Prior Publication Data
US 2009/0136604 A1 May 28, 2009

Related U.S. Application Data

(60) Provisional application No. 60/930,000, filed on Jul. 20, 2007.

(30) Foreign Application Priority Data

Jul. 17, 2007 (FR) .................................. 07 56551

(51) Int. Cl.
*A61K 8/00* (2006.01)
*A61K 35/74* (2006.01)
*A61Q 19/00* (2006.01)
(Continued)

(52) U.S. Cl.
CPC . *A61K 35/74* (2013.01); *A61K 8/99* (2013.01); *A61K 35/08* (2013.01); *A61Q 19/005* (2013.01); *A61K 2800/75* (2013.01)

(58) Field of Classification Search
CPC . A61K 35/08; A61K 2800/75; A01B 12/006; A61Q 19/005
See application file for complete search history.

(56) References Cited

U.S. PATENT DOCUMENTS

| | | |
|---|---|---|
| 4,419,449 A | 12/1983 | Maillard et al. |
| 5,795,574 A * | 8/1998 | Breton et al. .................. 424/115 |
| 6,190,671 B1 | 2/2001 | Aubert et al. |

(Continued)

FOREIGN PATENT DOCUMENTS

| | | |
|---|---|---|
| FR | 2693654 A1 | 1/1994 |
| FR | 2746646 A1 | 10/1997 |

(Continued)

OTHER PUBLICATIONS

The Water Company, Online, URL<http://dwb.unl.edu/Teacher/NSF/C01/C01Links/www.goodwaterco.com/comprob.htm>accessed Nov. 18, 2013, 31 pages.*

(Continued)

*Primary Examiner* — Patricia A Leith
(74) *Attorney, Agent, or Firm* — Buchanan Ingersoll & Rooney PC

(57) ABSTRACT

Sensitive skin, mucous membranes and scalps are treated by administering to individuals in need of such treatment, thus effective amounts of at least one extract of a non-photosynthetic and non-fruiting filamentous bacterium cultured in a medium which includes at least one non-sulfurous mineral and/or thermal water, e.g., an extract derived from the bacterium *Vitreoscilla filiformis*, in particular the strain ATCC 15551, cultured in a medium enriched with water from La Roche Posay.

16 Claims, 1 Drawing Sheet

(51) Int. Cl.
*A61K 8/99* (2006.01)
*A61K 35/08* (2015.01)

(56) References Cited

U.S. PATENT DOCUMENTS 6,242,229 B1* 6/2001 Pineau et al. ............ 435/170
2009/0136604 A1* 5/2009 Breton et al. ............ 424/780

FOREIGN PATENT DOCUMENTS

WO  WO 94/02158    *  2/1994
WO  WO 9402158     *  2/1994

OTHER PUBLICATIONS

Gueniche et al., "Improvement of atopic dermatitis skin symptoms by *Vitreoscilla filiformis* bacterial extract", EJD, Jul.-Aug. 2006, pp. 380-384, vol. 16, No. 4.

Desruelles et al., "Clinical evaluation of a skin care programme for acne-prone very oily skin demonstration of the activity of a *Vitreoscilla filiformis* extract of the phenomena of irritation and discomfort", Nouv. Dermatol., 2002, pp. 120-127, vol. 21.

Gueniche et al., "*Vitreoscilla filiformis* Bacterium Extract Improves Seborrheic Dermatitis", XP 009091787 2006 ESDR Abstracts, www.jidonline.org.

* cited by examiner

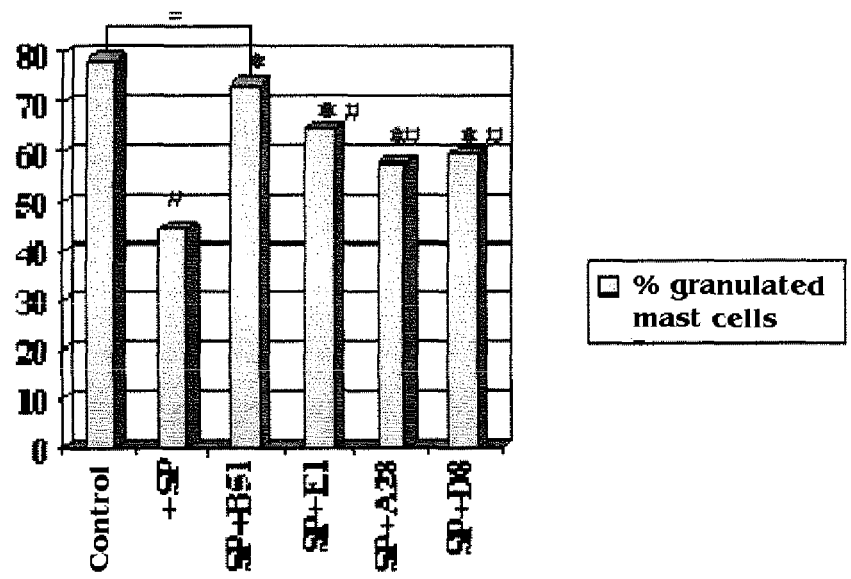

BACTERIAL EXTRACTS CULTURED IN THERMAL WATERS FOR TREATING SENSITIVE SKIN, MUCOUS MEMBRANES AND SCALPS

CROSS-REFERENCE TO COMPANION APPLICATIONS

Companion U.S. patent application Ser. No. 12/175,072; U.S. patent application Ser. No. 12/175,108; and U.S. patent application Ser. No. 12/175,119, filed concurrently herewith, each hereby also expressly incorporated by reference and each also assigned to the assignee hereof.

CROSS-REFERENCE TO PRIORITY/PROVISIONAL APPLICATIONS

This application claims priority under 35 U.S.C. §119 of FR 0756551, filed Jul. 17, 2007, and of U.S. Provisional Application No. 60/930,000, Jul. 20, 2007, each hereby expressly incorporated by reference and each assigned to the assignee hereof.

BACKGROUND OF THE INVENTION

1. Technical Field of the Invention

The present invention relates to the administration of bacterial extracts cultured in thermal water for the care of sensitive skin and/or scalps.

2. Description of Background and/or Related and/or Prior Art

Human skin is made up of two compartments, namely, a deep compartment, the dermis, and a surface compartment, the epidermis.

The epidermis is in contact with the external environment. One of its roles consists in protecting the body from dehydration and from external aggressions, especially linked to environmental factors of irritant or pollutant type (detergents, pollution, cigarette smoke, etc.), mechanical stresses (friction, abrasion, shaving, frequent washing, etc.), thermal or climatic imbalances (cold, wind, dryness, UV radiation, etc.), xenobiotics (microorganisms, allergens, etc.), cosmetic or dermatological chemical treatments (peeling, anti-acne treatment, etc.), or by physiological factors (age, stress, etc.).

Certain individuals have skin or a scalp that is more sensitive than others.

Generally, sensitive skin is defined by a particular reactivity of the skin. However, as opposed to skin that is qualified as allergic, this reactivity is not a matter of an immunological process, that is to say, does not occur only on skin that is already sensitized in response to the presence of an allergen. Its mechanism is said to be a specific.

This skin reactivity is conventionally expressed by the manifestation of signs of discomfort in response to contact of the subject with a triggering element which may have various origins. It may be the application of a cosmetic product to the surface of sensitive skin, the intake of food, the exposure to sudden temperature variations, to atmospheric pollution and/or to ultraviolet or infrared rays. There are also associated factors such as age and skin type. Thus, sensitive skin is more frequent among dry or greasy skin than among normal skin.

The appearance of these signs of discomfort, which appear in the minutes which follow the contact of the subject with the triggering element, is one of the main characteristics of sensitive skin. These are mainly dysesthesic sensations. The term "dysesthesic sensations" means more or less painful sensations that are felt in an area of the skin such as sensations of stinging, tingling, itching or pruritus, burning, hotness, discomfort, tautness, etc. These subjective signs usually exist in the absence of visible chemical signs such as redness and desquamations. It is known today that these skin irritation and intolerance reactions are especially linked to a release of neuropeptides by the nerve endings of the epidermis and of the dermis.

The exhibitions of sensitive skin or scalps in the meaning of the invention appear without any inflammatory reaction. It is known that inflammation is characterized by the four simultaneous clinical signs (robor, calor, dolor, tumor) which are not present the phenomenon of sensitive skin or scalps; in particular, there is no swelling (tumor) and the dysesthesic sensations, although uncomforting, could not be called painful.

For obvious reasons, the absence of visible signs makes the diagnosis of sensitive skin difficult. Usually, this diagnosis relies on taking a history from the patient. This symptomology moreover has the advantage of making it possible to differentiate sensitive skin associated or not with dry skin, from contact irritation or allergy for which there are, on the other hand, visible inflammatory signs.

Consequently, the development of "sensitive skin" products has made it necessary to use tools for evaluating the sensory reaction of the skin. The first tools were based, right from their design, on the essential feature of dry skin, namely, the presence of signs of discomfort induced by a topical application. Thus, the lactic acid "stinging test" was the first test proposed. It was carried out by recording the stinging sensations reported by a volunteer after application of a 10% lactic acid solution to the wings of the nose. The subjects reporting moderate or strong stinging sensations were referred to as "stingers" and considered to have sensitive skin. Due to this sensitivity of the skin to the topical application of a product, these subjects were then selected to test "sensitive skin" products. More recently, in order to specifically activate the peripheral nerve endings involved in the discomfort and known as nociceptors, recently identified as being involved in sensitive skin, new tests have been proposed which precisely use other inducers of discomfort such as capsaicin.

This second type of test, described in EP 1 374 913, also constitutes another tool that is particularly useful for the diagnosis of sensitive skin.

Within the meaning of the present invention, sensitive skin covers irritable skin and intolerant skin.

Intolerant skin is skin which reacts by sensations of hotness, tautness, tingling and/or redness, to various factors such as the application of cosmetic or dermatological products or of soap. In general, these signs are associated with erythema and with a hyperseborrhoeic or acneic skin, or even skin exhibiting rosacea, with or without dry patches.

Irritable skin is skin which reacts via pruritus, that is to say, via itching or via stinging, to various factors such as the environment, emotions, foods, wind, friction, shaving, hard water with a high calcium concentration, temperature variations or wool.

Usually, irritability of the skin is expressed by visible signs such as redness of the skin, a feeling of hotness of the skin or of the scalp (heat) which may extend to a feeling of pain.

"Sensitive" scalps have a more univocal clinical symptomology: the sensations of itching and/or of stinging and/or of hotness are mainly triggered by local factors such as friction, soap, surfactants, hard water with a high calcium concentration, shampoos or lotions. These sensations are also sometimes triggered by factors such as the environment, emotions and/or foods. An erythema and a hyperseborrhoea of the scalp and also a dandruff condition are frequently associated with the preceding signs.

Thus, need remains for novel compositions that make it possible to prevent and/or treat the symptoms of sensitive mucous membranes, scalps and skin.

SUMMARY OF THE INVENTION

A higher Substance P antagonist activity of a bacterial extract cultured in thermal water compared to the bacterial extract cultured conventionally has now been demonstrated.

Accordingly, this invention firstly features the cosmetic administration of at least one extract of a non-photosynthetic and non-fruiting filamentous bacterium cultured in a non-sulfurous thermal and/or mineral water as an agent for preventing and/or treating sensitive skin.

BRIEF DESCRIPTION OF THE DRAWING

The FIGURE of Drawing illustrates histological evaluation after staining with toluidine blue of the percentage of mast cells having a score of 3 (mean, n=8).

DETAILED DESCRIPTION OF BEST MODE AND SPECIFIC/PREFERRED EMBODIMENTS OF THE INVENTION

Bacterial Extract

The bacterial extracts according to the present invention are prepared according to a process comprising the culturing of at least one non-photosynthetic and non-fruiting filamentous bacterium in a medium comprising at least one non-sulfurous mineral and/or thermal water.

The bacteria are non-photosynthetic filamentous bacteria which comprise, in particular, the bacteria belonging to the order of the Beggiatoales and more particularly the bacteria belonging to the genera *Beggiatoa, Vitreoscilla, Flexithrix* or *Leucothrix*.

For implementing the invention, bacteria belonging to the genus *Vitreoscilla* are preferred, in particular bacteria of the species *Vitreoscilla filiformis*.

These bacteria, several of which have already been described, generally have an aquatic habitat and can be found in particular in sea waters or in thermal waters. Exemplary bacteria include:

*Vitreoscilla filiformis* (ATCC 15551)
*Vitreoscilla beggiatoides* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338)

Preferably, the bacterium is that corresponding to the strain deposited at the ATCC under No. 15551.

The term "thermal water" means a hot or cold water which is used for its therapeutic powers or for a bathing use. It is possible to use a thermal water or a mineral water. Generally, a mineral water is suitable for consumption, which is not always the case with a thermal water. Each of these waters comprises, inter alia, dissolved minerals and trace elements. These waters are known to be employed for specific treatment purposes depending on the particular trace elements and minerals present therein.

Preferably, a thermal and/or mineral water is employed which exhibits a total mineral content of greater than or equal to 400 mg/l.

According to this invention, the term "total mineral content" means the sum of the concentrations of anions and cations present in the thermal or mineral water. In the thermal or mineral waters according to the invention, the total mineral content generally ranges from 400 to 900 mg/l.

The thermal and/or mineral water according to the invention can have a total mineral content of at least 700 mg/l, in particular a total concentration of carbonates and of bicarbonates of at least 150 mg/l and more preferably of at least 360 mg/l and in particular of sodium carbonate and bicarbonate of greater than 2 mg/l. The concentration of silicon oxide in the water used in the composition according to the invention can preferably be at least 6 mg/l and more preferably at least 9 mg/l.

The thermal water or the mineral water according to the invention can be selected from water from Vittel, waters from the Vichy basin, water from Uriage, water from La Roche Posay, water from La Bourboule, water from Enghien-les-Bains, water from Saint-Gervais-les-Bains, water from Néris-les-Bains, water from Allevard-les-Bains, water from Digne, water from Maizières, water from Neyrac-les-Bains, water from Lons-le-Saunier, water from Eaux-Bonnes, water from Rochefort, water from Saint Christau, water from Les Fumades and water from Tercis-les-Bains.

Among these waters, those which exhibit a total concentration of carbonates or bicarbonates of greater than 360 mg/l are water from Vittel, water from La Bourboule, water from Les Fumades, water from Enghien-les-Bains, water from La Roche Posay, water from the Vichy basin and water from Uriage.

Among these waters, those which exhibit a concentration of carbonates or bicarbonates of from 150 mg/l and 360 mg/l are water from Digne, water from Maizières, water from Rochefort or water from Saint Gervais-les-Bains.

Among these waters, those which comprise at least 2 mg/l of sodium carbonate or bicarbonate are water from La Roche Posay, water from Vittel, waters from the Vichy basin or water from Uriage.

The waters comprising at least 9 mg/l of silicon oxide are water from La Roche Posay, water from Vittel, waters from the Vichy basin or water from Uriage.

The thermal or mineral waters which are particularly suitable for the implementation of the invention have a concentration of calcium ions of greater than or equal to 100 mg/l, indeed even 140 mg/l.

According to one advantageous embodiment, the thermal or mineral water has a concentration of hydrogencarbonate ions of greater than or equal to 300 mg/l. The hydrogencarbonates, also known as bicarbonates, are present in particular at a concentration of greater than or equal to 350 mg/l.

According to another advantageous embodiment, the bacteria are cultured in a medium comprising at least one thermal water. The latter can in particular be selected from water from Vittel, waters from the Vichy basin, water from Uriage, water from La Roche Posay, water from La Bourboule, water from Les Fumades, water from Enghien-les-Bains or water from Eaux-Bonnes.

The waters which make it possible to obtain a particularly advantageous result according to the invention are selected in particular from water from La Roche Posay and water from Vittel, or a water with a similar composition.

Water from La Roche Posay is extracted from the spring of the same name; it is a water comprising bicarbonate, calcium, silicate and selenium. It generally comprises approximately 387 mg/l of bicarbonate ions, approximately 140 mg/l of calcium ions and at least 4 mg/l of sulfates.

Water from Vittel is rich in calcium and in mineral salts (841 mg/l) and comprises in particular 202 mg/l of calcium, 402 mg/l of bicarbonates and 336 mg/l of sulfates.

Culturing can in particular be carried out in the following medium:

| Composition: | Concentration: |
|---|---|
| Autolyzed yeast extract | 0.5 to 5 g/l |
| Plant peptone | 0.5 to 5 g/l |
| Anhydrous glucose | 0.5 to 7 g/l |
| Heller microelements | 0.5 to 5 ml/l |
| $CaCl_2 \cdot 10H_2O$ | 0.010 to 0.200 g/l |

The composition is made up to 1,000 ml with mineral and/or thermal water optionally topped with distilled or osmosed water.

Exemplary peptones include soybean papain peptone.

This medium is distinguished from the media generally used by the absence of catalase and sulfide.

The Heller microelements have been described by Heller, *Ann. Sci. Nat. Biol. Veg.*, 14, 1-223 (1953). They are mixtures of various mineral elements which are recommended by Heller not for the culturing of bacteria but for the nutrition of plant tissues cultured in vitro.

Culturing can be carried out at the appropriate temperature suitable for the bacterial species cultured. Generally, this temperature ranges from 18 and 40° C., depending on the strains. The pH of the culture medium preferably ranges from 5.5 to 8.

The composition of the Heller microelements, per 1 l of water, is as follows:

| | |
|---|---|
| $ZnSO_4 \cdot 7H_2O$ | 1 g |
| $MnSO_4 \cdot H_2O$ | 0.076 g |
| $CuSO_4 \cdot 5H_2O$ | 0.003 g |
| KI | 0.010 g |
| $H_3BO_3$ | 1 g |
| $AlCl_3 \cdot 6H_2O$ | 0.050 g |
| $NiCl_2 \cdot 6H_2O$ | 0.030 g |

Said thermal or mineral waters can replace all or part of the aqueous phase of the culture medium. They can thus be a mixture in any proportion with the water, in particular distilled or osmosed water, present in the culture medium. The mixture (i) of thermal water and (ii) of osmosed or distilled water could be in a ratio from 0.1% to 100%, especially from 0.1 to 50, in particular from 0.1 to 25.

After mixing all the elements of the medium, the culture medium comprising the thermal and/or mineral water is advantageously sterilized; this stage is carried out by methods known to one skilled in the art, such as sterilization by filtration or by heat.

The culture medium is subsequently inoculated with the bacteria.

The media most suitable for culturing bacteria are such that the thermal or mineral water preferably is at least 0.1% of the amount of water introduced for the preparation of the medium, in particular from 0.1 to 99.9%. Good results are obtained with concentrations of thermal water of approximately 1.33%, with respect to the osmosed and/or distilled water, for example from 0.5 to 20%, indeed even from 0.5 to 50%, but these concentrations can be increased without disadvantage.

In known fashion, the process for preparing the bacterial extract comprises at least one stage in which the bacteria are recovered at the end of culturing, in particular by separating them from the culture medium.

After culturing the bacteria, the biomass can be isolated by various known methods, for example by filtration, by coagulation with an alcohol (ethanol, isopropanol, isobutanol), by drying on a cylinder with a scraped precoat (starch, diatoms, and the like) or by freeze-drying. A preliminary concentration, for example at 80° C. under reduced pressure, improves this separation.

The biomass may be used alive or else be treated by various processes. An operation of rupturing the envelopes can be carried out, for example by the action of ultrasound. In addition, extracts can be prepared using an alcohol, such as ethanol or propanol.

Lipopolysaccharide extracts can also be prepared according to known methods; for example, see Noris and Ribbons, *Methods in Microbiology*, Vol. 5B, Academic Press (1971). The method generally used is the well-known "Westphal" method (or a related method), which consists in carrying out the extraction with phenol/water mixtures at 65° C. The extract is subsequently subjected to dialysis in order to remove the phenol.

The bacterial extract employed according to the invention may also result from the implementation of the following process: (i) at least one bacterium belonging to the order of the Beggiatoales is cultured in a medium comprising a monosaccharide as main carbon source and at least one mineral or thermal water and then (ii), after fermentation, the bacteria are separated from the culture medium in order to recover said mass of bacteria.

The bacteria recovered on conclusion of the fermentation stage can in particular be subjected to a stabilization and/or extraction treatment. It is the extract of filamentous bacteria which is thus obtained which will generally be used in or for the preparation of cosmetic or dermatological compositions. In a way known per se, the extract can thus be sterilized, in particular by filtration or by autoclaving.

The term "extract of non-photosynthetic filamentous bacteria" means equally well the supernatant from the culturing of said bacteria, the biomass obtained after culturing said bacteria or the extracts of the biomass which are obtained by treatment of this biomass.

In order to prepare the extracts according to the invention, said bacteria can be cultured according to the above process and can then be separated from the biomass obtained, for example by filtration, centrifuging, coagulation and/or freeze-drying.

Thus, after culturing, the bacteria are concentrated by centrifuging. The biomass obtained is autoclaved. This biomass can be freeze-dried in order to constitute what is referred to as the freeze-dried extract. Any freeze-drying method known to one skilled in the art can be used to prepare this extract.

The supernatant fraction from this biomass can also be filtered into a sterile container in order to remove the suspended particles. This supernatant fraction can also be decanted under sterile conditions into a sterile container. According to a specific embodiment of the invention, the supernatant fraction thus obtained is used as cosmetic or dermatological active principle.

The bacterial extracts according to the invention may be formulated in a suitable carrier in an amount of at least 20% by weight relative to the total weight of the composition, in particular in an amount of 0.001 to 20% by weight relative to the total weight of the composition and more particularly in an amount of 0.01 to 10% by weight relative to the total weight of the composition.

For certain applications or specific formulations, it may be advantageous to use high weight concentrations of bacterial extract, for example from 15 and 20%.

The bacterial extract cultured in a medium enriched with thermal water may also be used in the form of fractions of cellular components or in the form of metabolites. The microorganism(s), metabolite(s) or fraction(s) may also be introduced in the form of a freeze-dried powder, a culture supernatant and/or, where appropriate, in a concentrated form.

For certain applications, the living biomass may be used as is, for example in the form of masks or a poultice for producing an immediate effect.

According to the invention, the term "metabolite" is any substance derived from the metabolism of the microorganisms considered according to the invention and endowed with an efficacy for treating dark circles.

Unexpectedly, it has now been observed that the bacterial extracts cultured in thermal water were able to prove effective for regulating vascularization defects of the contour of the eyes and thus to prevent and/or reduce bags and/or dark circles around the eyes.

Specifically, it has now been demonstrated that the extract of the bacterium *Vitreoscilla filiformis* cultured in thermal water from La Roche Posay has an increased effectiveness in treating vascular disorders compared to the extract of the same bacterium cultured in a conventional medium, that is to say, without mineral or thermal water.

The main difference from these two extracts is in the procedures for preparing the culture medium where there is substitution of osmosed water by water from La Roche Posay. This leads in particular to a modification of the metabolism of the bacteria caused by an enrichment of the culture medium in mineral elements, particularly in selenium, strontium and zinc.

It is also interesting to note that the introduction of this biomass into a formulatory carrier does not present a risk of overexposure to these elements, since Se and Zn are elements that are essential to the body and Sr is widespread in food.

The table below provides the concentrations of these chemical elements in the bacterial extract according to the invention prepared according to the procedure of Example 1 (freeze-dried extract).

| | |
|---|---|
| Se (mg/kg) | 6 |
| Sr (mg/kg) | 10 |
| Zn (mg/kg) | 216 |

Thus, the application of this enriched extract leads to topical exposures of mineral salts per day of around:

| | |
|---|---|
| Se (µg/day) | 0.008 |
| Sr (µg/day) | 0.0032 |
| Zn (µg/day) | 0.094 |

It is noted here that the use of ions for improving skin condition is very old. Thus, dermatologically-targeted thermal cures on the banks of the Dead Sea—the saltiest expanse of water in the world—go back to ancient times (Abels D J et col., *Clinics in Dermatol.*, 14: 653-658, 1996). These baths exert an anti-pruriginous activity and it is not uncommon that people treated experience the feeling of having smoother and more supple skin (Even-Pazz Z, Isr *J. Med. Sci.*, 32: 11-15, 1996). To date, the advantage of the topical application of cations has been studied as much in the field of sensitivity as in that of skin dryness. Among the divalent cations, it is the calming effect of strontium which has been most documented (Hahn G S, In biochemical modulation of skin reactions. Kydonieus A F, Will J J (eds.), CRE, Boca Raton, Fla., US, 261-272, 2000).

However, the ion-enrichment of the bacterial culture is not sufficient to explain the better properties of the extracts according to the invention, this is because the comparative tests carried out show a better activity of the bacterial extracts according to the invention compared to the same bacterial extracts cultured conventionally to which ions are added.

More specifically, the present invention features the cosmetic administration of at least one extract of a non-photosynthetic and non-fruiting bacterium cultured in a non-sulfurous thermal and/or mineral water as an agent for treating sensitive skin and scalps, especially intolerant or irritable skin.

Thus, the extracts according to the invention have an advantage as a calmative.

Unless otherwise indicated, the term "treating" means any action with a view to improving the comfort or the well-being of an individual, this term therefore equally covers preventing, attenuating, reducing, relieving and curing.

In particular, the present invention features the administration of at least one extract of a non-photosynthetic and non-fruiting bacterium cultured in a non-sulfurous mineral and/or thermal water as an agent for treating the dysesthesic sensations of sensitive skin, in particular the sensations selected from stinging and/or tingling and/or itching and/or hotness and/or skin discomfort and/or tautness of the skin.

The present invention also features the use of an effective amount of at least one extract of a non-photosynthetic and non-fruiting bacterium cultured in a non-sulfurous mineral and/or thermal water for preparing a composition useful to treat disorders associated with an excessive synthesis and/or release of Substance P, in particular skin disorders.

This invention also features at least one extract of a non-photosynthetic and non-fruiting bacterium cultured in a non-sulfurous mineral and/or thermal water for administration in the treatment of disorders associated with an excessive synthesis and/or release of Substance P, in particular skin disorders, and whether regime or regimen.

The compositions according to the invention are generally administered topically or orally, preferably orally.

The compositions according to the invention may be in any galenic form normally employed.

For a topical application, this is understood to be an application to the skin in the broad sense, that is to say, over any cutaneous surface of the body whether or not it is covered with body hair or head hair, especially a mucous membrane, semi-mucous membrane or scalp.

Such a topical application makes it possible to topically treat sensitive skin, including the lips and sensitive scalps, and signs which may be associated with it.

As regards the products useful to be applied topically with a view to producing the desired effect within the context of the invention, these may be aqueous, hydroalcoholic or oily solutions, dispersions of the solution type or dispersions of the lotion or serum type, emulsions of liquid or semi-liquid consistency of the milk type, suspensions or emulsions of the aqueous or anhydrous gel or cream type, microemulsions, microcapsules, microparticles or vesicular dispersions of ionic and/or non-ionic type.

The cosmetic and/or dermatological compositions, more particularly relating to a topical application, may especially be in the form of aqueous, hydroalcoholic or oily solutions, of dispersions of the solution type or dispersions of the lotion or serum type, of emulsions of liquid or semi-liquid consistency of the milk type, obtained by dispersion of a fatty phase in an aqueous phase (O/W) or vice versa (W/O), or of suspensions or emulsions of soft, semi-solid or solid consistency of the aqueous or anhydrous gel or cream type, or else microemulsions, microcapsules, microparticles, or vesicular dispersions of ionic and/or non-ionic type.

These compositions are prepared according to the usual methods.

These compositions may especially constitute creams for cleaning, protecting, treating or caring for the face, for the hands, for the feet, for the major anatomical folds or for the body (for example, day creams, night creams, makeup-removing creams, foundation creams, anti-sun creams), makeup products such as fluid foundations, makeup-removing milks, body protection or care milks, after-sun milks, skin care lotions, gels or foams, such as cleansing or disinfecting lotions, anti-sun lotions, artificial tanning lotions, bath compositions, deodorant compositions containing a bactericidal agent, aftershave gels or lotions, depilatory creams, or compositions for countering insect stings.

The compositions according to the invention may also consist of solid preparations constituting cleansing bars or soaps.

They may also be used for the hair in the form of aqueous, alcoholic or hydroalcoholic solutions or in the form of creams, gels, emulsions, foams or else in the form of aerosol compositions also containing a pressurized propellant.

When the composition of the invention is an emulsion, the proportion of the fatty phase may range from 5 to 80% by weight, and preferably from 5 to 50% by weight relative to the total weight of the composition. The oils, the emulsifiers and the co-emulsifiers used in the composition in emulsion form are selected from those conventionally used in the cosmetic and/or dermatological field. The emulsifier and the co-emulsifier may be present in the composition in an amount ranging from 0.3 to 30% by weight, and preferably from 0.5 to 20% by weight relative to the total weight of the composition.

When the composition of the invention is an oily gel or solution, the fatty phase may represent more than 90% of the total weight of the composition.

In known fashion, the cosmetic and/or dermatological composition of the invention may also contain adjuvants that are customary in the cosmetic, pharmaceutical and/or dermatological field, such as hydrophilic or lipophilic gelling agents, hydrophilic or lipophilic active agents, preservatives, antioxidants, solvents, fragrances, fillers, filters, bactericides, odor absorbers and dyestuffs. The amounts of these various adjuvants are those conventionally used in the field in question, and are for example from 0.01 to 20% of the total weight of the composition. These adjuvants, depending on their nature, may be introduced into the fatty phase and/or into the aqueous phase.

Of course, the compositions according to the invention may contain several other active agents.

By way of active agents that can be included in combination with the bacterial extract according to the invention, exemplary are vitamins B3, B5, B6, B8, C, E, or PP and niacin.

As hydrophilic active agents, it is possible to employ proteins or protein hydrolysates, amino acids, polyols, especially $C_2$ to $C_{10}$ polyols such as glycerol, sorbitol, butylene glycol and polyethylene glycol, urea, allantoin, sugars and sugar derivatives, water-soluble vitamins, starch, bacterial or plant extracts such as those from *Aloe vera*.

As lipophilic active agents, it is possible to employ retinol (vitamin A) and derivatives thereof, tocopherol (vitamin E) and derivatives thereof, ceramides and essential oils.

It is additionally intended to combine the active agents according to the invention with active agents especially intended for preventing and/or treating skin conditions.

According to another of its embodiments, the invention features compositions comprising at least one extract of a non-photosynthetic and non-fruiting bacterium cultured in a non-sulfurous mineral and/or thermal water in combination with at least one other neuropeptide inhibitor, especially a neuropeptide Y inhibitor, another Substance P antagonist, a GCRP antagonist, or else NO-synthase inhibitors and/or an ingredient capable of causing an irritation.

Examples of NO-synthase inhibitors that are suitable according to the present invention comprise, in particular, a plant extract of the species *Vitis vinifera* which is marketed, in particular, by Euromed under the trademark LEUCOCYANIDINES DE RAISONS EXTRA [grape leucocyanidins], or else by Indena under the trademark LEUCOSELECT®, or finally by Hansen under the trademark EXTRACT DE MARC DE RAISIN [grape marc extract]; a plant extract of the species *Olea europaea* which is preferably obtained from olive leaves and is especially marketed by Vinyals in the form of a dry extract, or by Biologia & Technologia under the trademark EUROL BT; and an extract of a plant from the species *Ginkgo biloba* which is preferably a dry aqueous extract of this plant marketed by Beaufour under the trademark GINKGO BILOBA EXTRAIT STANDARD [*Ginkgo biloba* standard extract].

The compositions according to the invention comprising an NO-synthase inhibitor as defined above may advantageously be used to prevent or treat the signs of skin aging and/or sensitive skins.

Among the compounds capable of causing a skin irritation, exemplary are cosmetic compounds or active agents, dermatological compounds or active agents, surfactants, in particular anionic surfactants, preservatives, detergents, fragrances, and in particular fragrancing alcoholic solutions, solvents and propellants, and mixtures thereof.

More particularly, by way of dermatological or cosmetic active agents, exemplary are certain desquamating agents which may also be peeling agents.

Among the agents specifically for peeling, exemplary are abrasive/exfoliating particles of mineral, organic, natural or synthetic sources. Particularly exemplary are pumice stone particles, silica particles, polyethylene beads, nylon beads and fruit kernel powders.

Among these desquamating agents, the following are capable of causing a skin irritation: saturated monocarboxylic acids (acetic acid) and unsaturated monocarboxylic acids, saturated and unsaturated dicarboxylic acids, saturated and unsaturated tricarboxylic acids; α-hydroxy acids and β-hydroxy acids of monocarboxylic acids; α-hydroxy acids and β-hydroxy acids of dicarboxylic acids; α-hydroxy acids and β-hydroxy acids of tricarboxylic acids, keto acids, α-keto acids or β-keto acids of polycarboxylic acids, of polyhydroxy monocarboxylic acids, of polyhydroxy dicarboxylic acids and of polyhydroxy tricarboxylic acids.

Among the α-hydroxy acids or esters thereof, exemplary are: glycolic acid, dioic acids, for instance octadecenedioic acid or ARLATONE DIOC DCA marketed by Uniqema, citric acid, lactic acid, tartaric acid, malic acid or mandelic acid, and esters thereof, such as dialkyl (C12/C13) tartrate or COSMACOL ETI, and branched C12-13 trialcohol citrate or COSMACOL ECl marketed by Sasol.

Among the β-hydroxy acids, exemplary are: salicylic acid and derivatives thereof (including 5-n-octanoylsalicylic acid).

Among the α-keto acids, exemplary are ascorbic acid and derivatives thereof.

Among the other desquamating agents, exemplary are: pyruvic acid, gluconic acid, glucuronic acid, oxalic acid, malonic acid, succinic acid, acetic acid, gentisic acid, cinnamic acid, azelaic acid; phenol; resorcinol; urea and derivatives thereof, hydroxyethyl urea or HYDROVANCE® from National Starch; oligofucoses; jasmonic acid and derivatives thereof; ascorbic acid and derivatives thereof, trichloroacetic acid; extract of *Saphora japonica* and *resveratrol*.

Among the desquamating agents, those capable of acting on the enzymes involved in desquamation or corneodesmosome degradation may also be capable of causing a skin irritation.

Among these, in particular exemplary are mineral salt chelating agents such as EDTA; N-acyl-N,N',N'-ethylenediaminetriacetic acid; aminosulfonic compounds, and in particular (N-2-hydroxyethylpiperazin-N-2-ethane)sulfonic acid (HEPES); derivatives of 2-oxathiazolidine-4-carboxylic acid (procysteine); derivatives of α-amino acids of glycine type (as described in EP 0 852 949, and also sodium methyl glycine diacetate marketed by BASF under the trademark TRILON M®); honey; and sugar derivatives such as O-octanoyl-6-D-maltose, O-linoleyl-6-D-glucose and N-acetyl-glucosamine.

Retinoids are also compounds capable of causing a skin irritation. Examples thereof include retinol and esters thereof, retinal, retinoic acid and derivatives thereof such as those described in FR-A-2 570 377, EP-A-199 636, EP-A-325 540 and EP-A-402 072, and adapalene.

The salts and derivatives, such as the cis or trans forms, the racemic mixtures and the dextrorotatory or levorotatory forms of the compounds indicated above are also considered to be compounds capable of causing a skin irritation.

Other dermatological or cosmetic active agents capable of causing a skin irritation are also mentioned below:

urea and derivatives thereof, such as hydroxyethylurea or HYDROVANCE® from National Starch, certain vitamins such as vitamin D and derivatives thereof such as vitamin D3 or vitamin D2, calcitriol, calcipotriol, tacalcitol, 24,25-diOH vitamin D3, 1-OH vitamin D2 and 1,24-diOH vitamin D2; vitamin B9 and derivatives thereof, peroxides such as benzoyl peroxide or aqueous hydrogen peroxide, agents for combating hair loss, such as minoxidil and derivatives thereof such as aminexil, hair dyes and hair colorants, such as aminophenols and derivatives thereof such as para-phenylenediamine (p-PDA), N-phenyl p-PDA, 2,5-toluenediamine sulfate, meta-phenylenediamine (m-PDA), 3,4-toluenediamine and ortho-phenylenediamine (o-PDA), antiperspirants, for instance aluminum salts such as aluminum hydroxychloride, deodorants, hair-removing and/or permanent-waving active agents such as thioglycolates or aqueous ammonia, thioglycolate and salts thereof, phenoxyethanol, 1,2-pentanediol, fragrancing alcoholic solutions (fragrances, eaux de toilette, aftershaves or deodorants), anthralins (dioxyanthranol), anthranoids (for example, those described in document EP-A-319028), lithium salts, depigmenting agents (for example: hydroquinone, vitamin C at high concentration, kojic acid), certain slimming active agents with a heating effect, nicotinates and derivatives thereof, capsaicin, anti-louse active agents (pyrethrin), anti-proliferative agents such as 5-fluorouracil or methotrexate, antiviral agents, anti-parasitic agents, antifungal agents, anti-pruriginous agents, anti-seborrhoeic agents, certain sunscreens, propigmenting agents such as psoralenes and methylangecilines, and mixtures thereof.

As preservatives, exemplary are phenoxyethanol, chlorhexidine and benzalkonium chloride.

As surfactants, exemplary are anionic, cationic and amphoteric surfactants, more particularly anionic surfactants such as alkyl sulfates and alkyl ether sulfates, for instance lauryl sulfate and lauryl ether sulfate, and salts thereof, in particular the sodium salts thereof.

According to a preferred embodiment of the invention, the compound capable of causing a skin irritation is selected from among retinoids, α-hydroxy acids, β-hydroxy acids, saturated and unsaturated dicarboxylic acids such as octadecenedioic acid or ARLATONE DIOC DCA marketed by Uniqema, anionic, cationic or amphoteric surfactants, 5-n-octanoylsalicylic acid, antiperspirant active agents such as aluminum salts, (N-2-hydroxyethylpiperazine-N-2-ethane) sulfonic acid (HEPES) and cinnamic acid.

The compound capable of causing a skin irritation may be present in the composition according to the present invention in an amount sufficient to cause a skin irritation reaction. By way of example, it may be present at a content ranging from 0.0001% to 70% by weight, preferably from 0.01% to 50% by weight, and better still from 0.1% to 30% by weight, relative to the total weight of the composition.

According to another embodiment, the present invention features a cosmetic regime or regimen for treating sensitive skin and/or mucous membranes and/or semi-mucous membranes and/or scalps which may be carried out in particular by applying the compositions such as defined above according to the customary usage technique of these compositions. For example: by application, that is to say, by topically spreading over an area of the body, or even by massaging in order to make creams, gels, serums, lotions, makeup-removing milks or after-sun compositions penetrate into the skin or into dry hair, application of a hair lotion to wet hair, of shampoos, or else application of toothpaste to the gums.

The method according to the invention may comprise a single administration. According to another embodiment, the administration is repeated, for example 2 to 3 times daily over one day or longer and generally over a prolonged duration of at least 4 weeks, or even 4 to 15 weeks, with, where appropriate, one or more periods of interruption.

This method is advantageously carried out before and/or after a step of mechanical or chemical peeling, of exfoliation of the skin. This is because, due to its calming properties, the bacterial extract according to the invention prevents, relieves or treats any discomfort reaction such as dysesthesic sensations or signs of irritation.

According to one embodiment of the invention, the method additionally comprises a step of peeling or of abrasion of the skin.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Preparation of a Bacterial Extract According to the Invention: Biomass of *Vitreoscilla filiformis* Cultured in a Medium Enriched with Thermal Water from La Roche Posay Preparation of the Culture Medium:
Composition:

| Yeast extract | 2 to 3 g |
|---|---|
| Soybean papain peptone | 2 to 3 g |
| Glucose | 2 to 3 g |
| Heller microelements | 2 ml |
| $CaCl_2 \cdot 2H_2O$ | 66.21 mg |
| Thermal water from La Roche Posay | 13-14 ml |

This stock solution will be diluted with osmosed water in a ratio of 1/75 before sterilization.

The pH of the medium is adjusted to 5.00 by adding a molar solution of $H_3PO_4$. The medium is sterilized by autoclaving at 121° C. for 30 minutes. After cooling to ambient temperature, the pH is readjusted to 7.20 by adding a molar solution of KOH.

Culturing:

After the medium has been inoculated at 1% with the *Vitreoscilla filiformis* strain deposited at the ATCC under No. 15551, the culture is shaken on an orbital shaker at 100 rpm and at 26° C. After growth for 48 hours, the culture is centrifuged at 8,000 g for 15 minutes. The pellets are recovered and then autoclaved at 121° C. for 30 minutes. This biomass can be used for evaluation tests.

Example 2

Activity of the Bacterial Extract According to the Invention (Biomass of *Vitreoscilla filiformis* Cultured in a Medium Enriched with Thermal Water from La Roche Posay)

The ability of such a biomass cultured in a thermal water (water from La Roche Posay) to adjust the neurogenic inflammation has been achieved.

Experimental Results for Four Products Evaluated:

The products evaluated are the following:

D8: biomass of *Vitreoscilla filiformis* cultured in a medium supplemented with Sr, Se and Zn;

B51: biomass of *Vitreoscilla filiformis* cultured in a medium enriched with thermal water from La Roche Posay;

A28: biomass of *Vitreoscilla filiformis* cultured in an osmosed $H_2O$ medium; and E1: biomass of *Vitreoscilla filiformis* cultured in a medium supplemented with Sr.

The FIGURE of Drawing shows that the 4 preparations are statistically different compared to the skin treated by Substance P.

The fraction B51 is the only one which restores normal function.

*$p<0.05$ versus treated skin/# $p<0.05$ versus skin treated with Substance P

It is thus observed that the treatment of a human skin explant under survival conditions with a biomass of *Vitreoscilla filiformis* cultured in a medium enriched with thermal water from La Roche Posay completely protects the tissue from mast cell degranulation and from the release of histamine which follows a neurogenic stress induced by Substance P.

To the contrary, the biomass cultured in the same culture medium obtained with distilled water only has a less significant activity over this neurogenic process.

Thus, the biomass of *Vitreoscilla filiformis* cultured in a medium enriched with thermal water from La Roche Posay has a protective activity that is statistically greater to such a point that the skin stressed artificially by the Substance P can no longer be distinguished from an unstressed skin in the presence of the bacterial extract according to the invention.

Example 3

Compositions

Facial Lotion for Sensitive Skin:

| Extract according to Example 1 | 5.00 |
|---|---|
| Magnesium gluconate | 3.00 |
| Calcium lactate | 2.00 |
| Antioxidant | 0.05 |
| Isopropanol | 40.0 |
| Preservative | 0.30 |
| Water | qs 100% |

Facial Care Gel for Sensitive Skin:

| Strontium nitrate | 4.00 |
|---|---|
| Powder of a biomass of *Vitreoscilla filiformis* cultured in a medium enriched with thermal water from La Roche Posay | 5.00 |
| Hydroxypropyl cellulose (KLUCEL H ® marketed by Hercules) | 1.00 |
| Vitamin E | 2.50 |
| Antioxidant | 0.05 |
| Isopropanol | 40.00 |
| Preservative | 0.30 |
| Water | qs 100% |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological method for treating skin, mucous membranes, the scalp or a combination thereof, the method comprising:

making a culture medium; which comprises adding (a) osmosed and/or distilled water and (b) a second water comprising a total concentration of carbonates or bicarbonates of at least 150 mg/l, at least 6 mg/l of silicon oxide, greater than or equal to 100 mg/l of calcium ions and at least 4 mg/l of sulfates; wherein (b) is added in a range of 0.5 to 50% based on the amount of osmosed and/or distilled water of (a);

culturing a non-photosynthetic and non-fruiting filamentous bacterium in said medium to produce a cultured non-photosynthetic bacterium in said medium;

preparing a composition comprising between 0.001% and 20% by weight of an extract of said cultured bacterium; and administering said composition to skin, mucous membranes, scalp or a combination thereof of an individual; wherein said non-photosynthetic and non-fruiting filamentous bacterium is selected from the group consisting of *Vitreoscilla filiformis, Vitreoscilla beggiatoides, Beggiatoa alba, Flexithrix dorotheae, Leucothrix mucor* and *Sphaerotilus natans*.

2. The cosmetic/dermatological method as defined by claim 1, said non-photosynthetic and non-fruiting filamentous bacterium comprising:

*Vitreoscilla filiformis* (ATCC 15551);
*Vitreoscilla beggiatoïdes* (ATCC 43181);
*Beggiatoa alba* (ATCC 33555);
*Flexithrix dorotheae* (ATCC 23163);
*Leucothrix mucor* (ATCC 25107); or
*Sphaerotilus natans* (ATCC 13338).

3. The cosmetic/dermatological method as defined by claim 1, said second water having a total mineral content ranging from 400 to 900 mg/l.

4. The cosmetic/dermatological method as defined by claim 1, said second water having a total concentration of carbonates and of bicarbonates of at least 360 mg/l and at least 9 mg/l of silicon oxide.

5. The cosmetic/dermatological method as defined by claim 1, wherein said composition comprises from 0.001 to 20% by weight of said cultured bacterium.

6. The cosmetic/dermatological method as defined by claim 1, wherein making said medium further comprises adding autolyzed yeast extract, plant peptone, anhydrous glucose, Heller microelements and calcium chloride.

7. The cosmetic/dermatological method as defined by claim 1, wherein said extract of cultured bacterium comprises selenium, zinc or strontium.

8. The cosmetic/dermatological method as defined by claim 1, wherein administering comprises topical application.

9. The cosmetic/dermatological method as defined by claim 1, wherein the non-photosynthetic and non-fruiting filamentous bacterium comprises *Vitreoscilla filiformis*.

10. The cosmetic/dermatological method as defined by claim 1, wherein making said medium further comprises adding yeast extract, soybean papain peptone, glucose, Heller microelements and $CaCl_2.2H_2O$.

11. The cosmetic/dermatological method as defined by claim 1, wherein the composition administered further comprises at least one agent selected from the group consisting of vitamin B3, vitamin B5, vitamin B6, vitamin B8, vitamin C, vitamin E and derivatives thereof, retinol (vitamin A), retinol derivatives, niacin, proteins, protein hydrolysates, amino acids, polyols, urea, allantoin, sugars, sugar derivatives, starch, bacterial or plant extracts, ceramides and essential oils.

12. The cosmetic/dermatological method as defined by claim 11, wherein said composition comprises polyols and wherein said polyols are selected from the group consisting of glycerol, sorbitol, butylene glycol and polyethylene glycol.

13. The cosmetic/dermatological method as defined by claim 11, wherein said composition comprises a plant extract and wherein said plant extract is *aloe vera*.

14. The cosmetic/dermatological method as defined by claim 1, wherein the composition administered further comprises water-soluble vitamins.

15. The cosmetic/dermatological method as defined by claim 1, wherein the composition administered comprises an agent selected from the group consisting of vitamins, peroxides, hair dyes, hair colorants, antiperspirants, deodorants, hair removing agents, permanent-wave agents for hair, alcoholic fragrances, anthralins, anthranoids, lithium salts, depigmenting agents, slimming active agents, nicotinates, capsaicin, anti-louse active agents, anti-proliferative agents, antiviral agents, anti-parasitic agents, anti-fungal agents, anti-pruriginous agents, anti-seborrheic agents, sunscreens, propigmenting agents, preservatives, surfactants, skin irritants, desquamating agents and nitric oxide (NO) synthase inhibitors, cosmetic carriers and dermatological carriers.

16. The cosmetic/dermatological method as defined by claim 1, wherein said composition is in the form of a: cream, bar, soap, solution, gel, foam, aerosol, serum, lotion, shampoo or toothpaste.

* * * * *